(12) United States Patent
Vu et al.

(10) Patent No.: US 11,397,470 B2
(45) Date of Patent: Jul. 26, 2022

(54) TONGUE LOCALIZATION, TEETH INTERACTION, AND DETECTION SYSTEM

(71) Applicant: The Regents of the University of Colorado, Denver, CO (US)

(72) Inventors: Tam Vu, Boulder, CO (US); Phuc Nguyen, Denver, CO (US); Nam Bui, Broomfield, CO (US); Robin Deterding, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 251 days.

(21) Appl. No.: 16/875,808

(22) Filed: May 15, 2020

(65) Prior Publication Data
US 2020/0363871 A1    Nov. 19, 2020

Related U.S. Application Data

(60) Provisional application No. 62/849,325, filed on May 17, 2019.

(51) Int. Cl.
| | |
|---|---|
| *G06F 3/01* | (2006.01) |
| *A61B 5/00* | (2006.01) |
| *A61B 5/11* | (2006.01) |
| *A61B 5/369* | (2021.01) |
| *A61B 5/394* | (2021.01) |

(52) U.S. Cl.
CPC ............ *G06F 3/015* (2013.01); *A61B 5/1107* (2013.01); *A61B 5/369* (2021.01); *A61B 5/394* (2021.01); *A61B 5/4547* (2013.01); *A61B 5/4552* (2013.01); *A61B 5/7246* (2013.01); *G06F 3/017* (2013.01)

(58) Field of Classification Search
CPC ......... G06F 3/015; A61B 5/394; A61B 5/369; A61B 5/1107
USPC ........................................ 345/156, 173, 174
See application file for complete search history.

(56) References Cited

U.S. PATENT DOCUMENTS

| | | | | |
|---|---|---|---|---|
| 5,212,476 | A * | 5/1993 | Maloney | A61B 5/394 455/100 |
| 2009/0309747 | A1* | 12/2009 | Ghovanloo | A61F 4/00 340/686.1 |
| 2014/0342324 | A1* | 11/2014 | Ghovanloo | G09B 5/06 434/185 |
| 2019/0057700 | A1* | 2/2019 | Kent | G06F 3/167 |

* cited by examiner

*Primary Examiner* — Calvin C Ma

(57) ABSTRACT

A computer-implemented method for identifying tongue movement comprises detecting an electroencephalography ("EEG") signal from an EEG sensor. The EEG sensor is configured to sense the EEG signal generated by a brain in association with a tongue movement. The method also comprises detecting the EMG signal from the EMG sensor. The EMG sensor is configured to sense the EMG signal generated by cranial nerve stimulation of muscles associated with the tongue movement. The method also includes identifying the tongue movement based on the EEG signal and the EMG signal. The method then includes correlating the tongue movement with one of a plurality of tongue location areas.

20 Claims, 21 Drawing Sheets

| Teeth Area ID | Description |
|---|---|
| 1,2 | inside/outside the lower teeth on the left |
| 3 | outside the lower teeth in the front |
| 4,5 | inside/outside the lower teeth on the right |
| 6,7 | inside/outside the upper teeth on the left |
| 8 | outside the upper teeth in the front |
| 9,10 | inside/outside the upper teeth on the right |

TONGUE LOCALIZATION, TEETH INTERACTION, AND DETECTION SYSTEM

CROSS-REFERENCE TO RELATED APPLICATIONS

This application claims the benefit of and priority to U.S. Provisional Patent Application Ser. No. 62/849,325 filed on 17 May 2019 and entitled "Tongue Localization, Teeth Interaction, And Detection System," which application is expressly incorporated herein by reference in its entirety.

GOVERNMENT RIGHTS

This invention was made with government support under grant number 1602428 awarded by the National Science Foundation. The government has certain rights in the invention.

BACKGROUND OF THE INVENTION

1. Technical Field

Wearable devices to capture the relative location or interaction between a wearer's tongue and teeth and computer implemented interfaces for tongue location recognition or tongue-on-teeth typing.

2. Background and Relevant Art

Computers and computing systems have affected nearly every aspect of modern living. Computers are generally involved in work, recreation, healthcare, transportation, entertainment, household management, etc. As computers have become increasingly vital to daily life, there has been great interest in exploring new ways of interacting with computer systems. For example, significant interest and research has gone into voice-based computer interactions, which allow users to interact with a computer system using only normal human verbal commands.

While these innovations in computer-to-human interfacing have been valuable, there is still significant work needed in identifying and developing novel ways to interact with a computer. In particular, there is interest in exploring human-to-computer interfacing that allows individuals with disabilities to more fully participate within the modern, computer-based society.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF THE INVENTION

The present invention can comprise systems, methods, and apparatus configured for identifying tongue movement. The systems, methods, and apparatus detect an electroencephalography ("EEG") signal from an EEG sensor. The EEG sensor is configured to sense the EEG signal generated by a brain in association with a tongue movement. The systems, methods, and apparatus also detect the EMG signal from the EMG sensor. The EMG sensor is configured to sense the EMG signal generated by cranial nerve stimulation of muscles associated with the tongue movement. The SKD sensor is configured to sense the skin surface deformation caused by the tongue movement. The systems, methods, and apparatus identify the skin surface deformation from the SKD sensor. The systems, methods, and apparatus identify the tongue movement based on the EEG signal, the EMG signal, and the SKD signal. The systems, methods, and apparatus then correlate the tongue movement with one of a plurality of tongue location areas.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above recited and other advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings.

DETAILED DESCRIPTION OF THE PREFERRED EMBODIMENTS

The present invention extends to systems, methods, and apparatus configured for identifying tongue movement. The systems, methods, and apparatus detect an electroencephalography ("EEG") signal from an EEG sensor. The EEG sensor is configured to sense the EEG signal generated by a brain in association with a tongue movement. The systems, methods, and apparatus also detect the EMG signal from the EMG sensor. The EMG sensor is configured to sense the EMG signal generated by cranial nerve stimulation of muscles associated with the tongue movement. The SKD sensor is configured to sense the skin surface deformation caused by the tongue movement. The systems, methods, and apparatus identify the skin surface deformation from the SKD sensor. The systems, methods, and apparatus identify the tongue movement based on the EEG signal, the EMG signal, and the SKD signal. The systems, methods, and apparatus then correlate the tongue movement with one of a plurality of tongue location areas.

Figure 1:
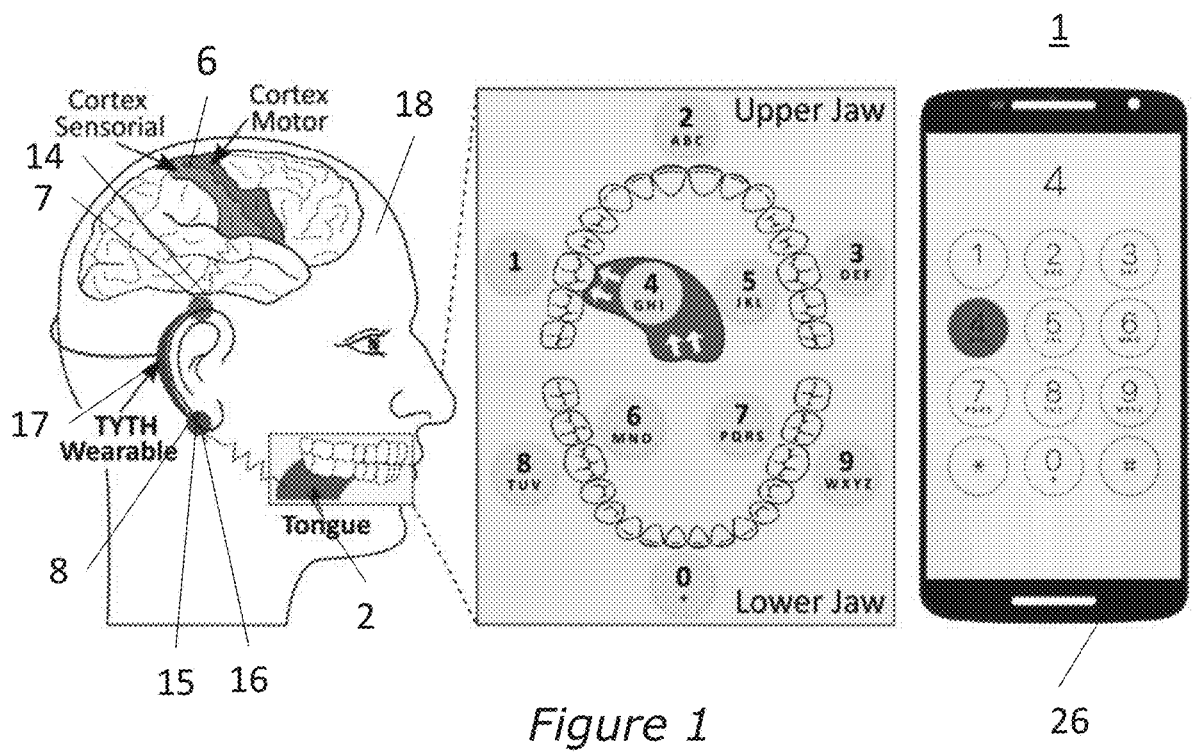
FIG. 1 is an illustration overview of a tongue-on-teeth typing system.
Figure 2:
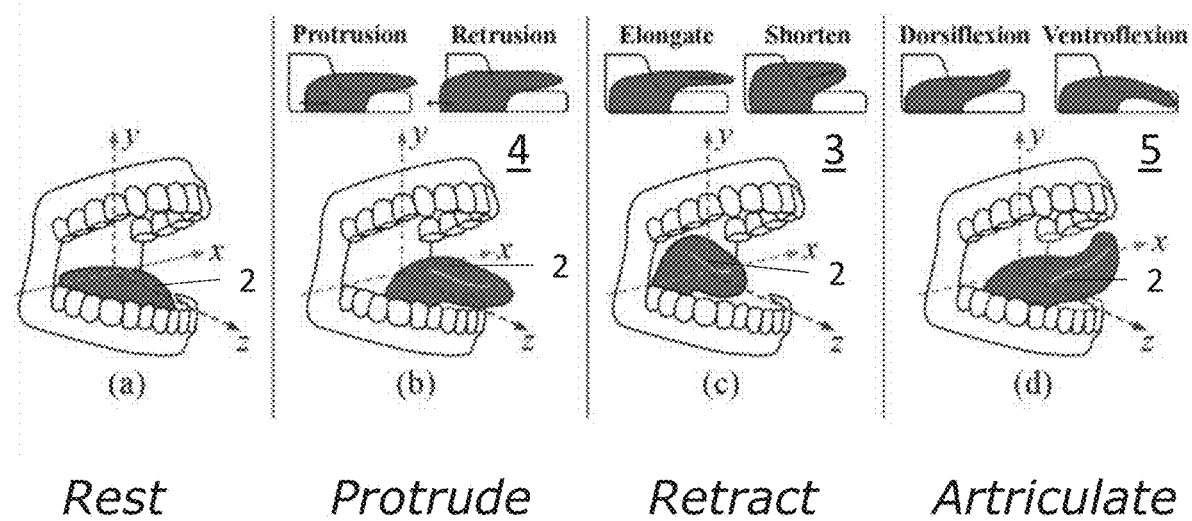
FIG. 2 is an illustration of tongue movement classified into four broad categories.

Now referring primarily to FIGS. 1 and 2, the tongue (2) is one of the most complex anatomical structures of the human body. For the purposes of this invention tongue movement can be classified into three broad categories or patterns: 1) retract, 2) protrude and 3) articulate which can be further classified into different categories as shown in the example of FIG. 2.

Now referring primarily to FIG. 2, a retract pattern (3) can be characterized by the posterior movement of the tongue with limited change in shape. It is mediated by the extrinsic muscles, specifically the hyoglossus (HG) (10) or the styloglossus (SG) (11), or a combination thereof. Both of these muscles receive input from the hypoglossal (CN XII) cranial nerve. This retraction results in the shortening of the blade of the tongue which is oriented lengthwise and can be attributed to the superior longitudinal (SL) or inferior longitudinal (IL) muscles, or combinations thereof. For the purposes of this invention, the posterior movement of the tongue refers to retraction and the anterior movement of the muscles refers to protrusion.

Again, referring primarily to FIG. 2, a protrusion pattern (4) can be caused by the posterior fascicles of the genioglossus muscle (GG) (12) muscle. The GG muscle is the largest muscle in the tongue musculature and is innervated by the hypoglossal cranial nerve (CN). Protrusion of the tongue can be caused by contraction of the vertical or transverse (TV) muscles, or combinations thereof.

Again, referring primarily to FIG. 2, an articulate pattern (5) includes tongue movements mostly associated with the motor function of articulation. Dorsiflexion can be characterized by the superior bending of the tongue tip caused by the contraction of the superior longitudinal (SL) muscle. Ventroflexion can be characterized by inferior bending of the tongue tip caused by contractions of inferior longitudinal (IL) muscles. Retroflexion can be characterized as the superior movement of the tongue base, which combines the superior and posterior pull of the SG muscle (11) aided by depression of the mid tongue by vertically oriented muscle fascicles of the GG (12). Characterization of these tongue movement patterns defines certain tongue postures, tongue location in relation to the teeth, or tongue pressing on pressing locations on the teeth.

Each different tongue movement, location of the tongue in relation to the teeth, or pressing of the tongue on pressing locations on the teeth can trigger different types of biological signals. These biological signals can include electric potentials emanating from brain or muscles cells, or combinations thereof. Examples of biological signals include the following:

Firstly, the electrical activity in the brain generates an EEG signal. A group of neurons when active produce an electrical field potential which can be measured on the skin as an EEG signal. Secondly, the muscles involved in the movement of tongue (9) include one or more, but are not necessarily limited to, HG, GG, SG, or TV. The electrical activity in response to a nerve's stimulation of the muscle or just the muscle response can be measured on the skin as an EMG signal. Thirdly, during tongue movement, the skin surface can drastically deform at certain locations on the human face. This skin surface deformation can be used to identify tongue location and direction. A skin surface deformation can be measured on the skin as a SKD signal.

Figure 3:
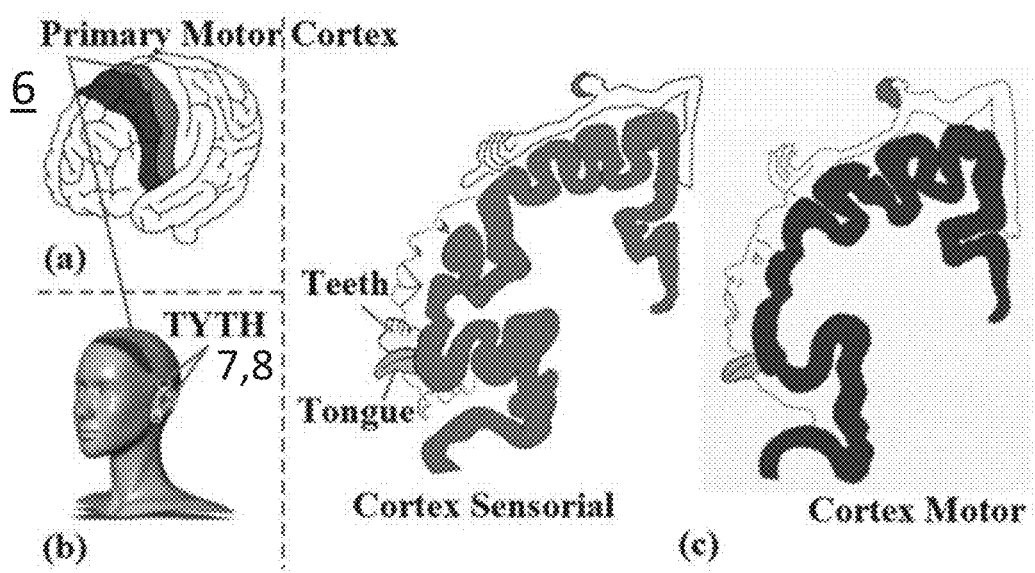
FIG. 3 is an illustration of the locations for capture of electroencephalogram (EEG), electromyography (EMG), and skin deformation (SKD) signals.

Now referring primarily to FIG. 3, the EEG, EMG, and SKD signals generated by tongue movement, tongue location, or tongue pressing (also referred to as "tongue tapping") on a pressing surface of the teeth (also referred to as "teeth area") can be processed and analyzed to identify the teeth area (13) tapped by the tongue. These three main signals can be captured at different locations or positions on the human head. In particular embodiments, behind the back of the outer ear can, but need not necessarily be, the best location to place one or more EEG sensors. This may be because the skin behind the back of the outer ear has proximity to both the brain EEG signal source controlling tongue movement (the primary motor cortex), and the muscles involved in tongue movement (e.g., HG (10), SG (11)).

Again, referring primarily to FIG. 3, the primary motor cortex (6) can control tongue movement by innervating hypoglossal, vagus and facial cranial nerves. The primary motor cortex (5) has a location in the frontal lobe of the brain along the precentral gyrus. Movement of the tongue can be associated with firing of neurons on the primary motor cortex which receives somatosensory information through the efferent fibers of the tongue. The firing of neurons creates an electric field potential which can be measured on the skin using EEG sensors (14). Additionally, significant scalp potential can be caused by modest tongue movements. In some embodiments, scalp potential may have the highest density near the ear canals and the orbital fossae. The EEG signal related to human tongue movement can be about 10 Hz to about 40 Hz. EEG sensors can, but need not necessarily be, positioned on the skin behind the top of outer ear (7) (as shown in the examples of FIGS. 1 and 3 to capture EEG signals associated with tongue movement, tongue location, or tongue pressing on pressing locations on the teeth. In preferred embodiments, the EEG sensor(s) can be positioned on the skin behind the top of outer ear (7).

Figure 4:
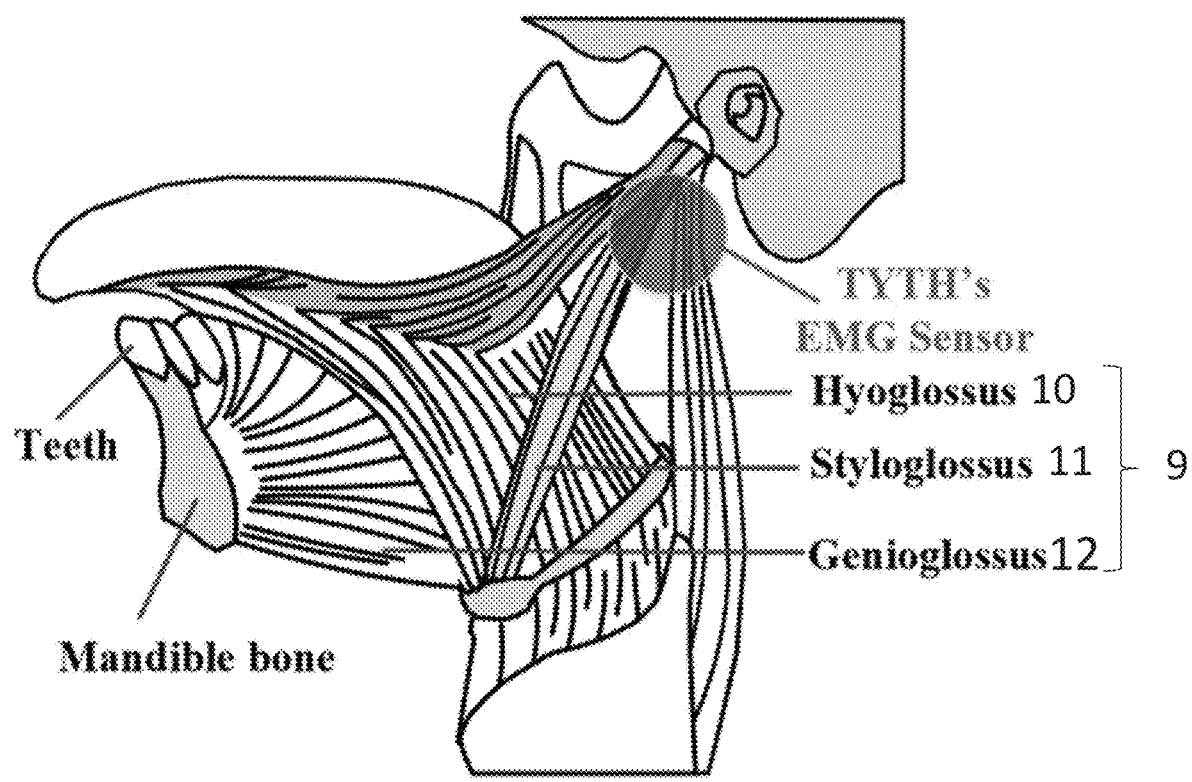
FIG. 4 is an illustration of the tongue extrinsic muscles behind the outer ear.

Now referring primarily to FIG. 4, the tongue's extrinsic muscles (9) are attached to the hyoid bone, located in the anterior midline of the neck between the chin and thyroid cartilage. In particular embodiments, the hyoid EMG signal can be captured. Additionally, in particular embodiments, the electrical activity in the cranial nerves in addition to hyoid EMG signal can be measured. Accordingly, EMG sensor(s) can be located to capture the evoked potential due to the signals that innervate the different muscle movements. In preferred embodiments, EMG sensor(s) (15), shown in FIG. 5, can be position behind the bottom of the outer ear where nerves originating from the brain start converging towards the hyoid bone. Behind the bottom of the outer ear (8) the EMG sensor(s) (15) can capture the EMG signals from HG (10) and SG (11) muscles. Even though these two are not fully connected with the tongue intrinsic muscle, as the GG (12) muscle, the EMG signals generated by tongue movement can be clearly captured by an EMG sensor(s) (15) positioned behind the outer ear below to the ear canal.

Again, referring primarily to FIG. 4, muscle contraction during tongue movement creates skin surface deformation. More specifically, the relaxation or contraction of HG and SL muscles expands or compresses the skin surface where the jaw bone is connected to the human head. Such surface deformation happens strongly at the gap between the lower jaw and the head. In particular embodiments the SKD sensor(s) (16), shown in FIGS. 1 and 9, can be placed behind the bottom of the outer ear to capture SKD signals. In particular embodiments, the EMG sensor(s) (15) and the SKD sensor(s) (16) can be substantially co-located behind the bottom of the outer ear (8) to capture SKD signals.

Figure 5:
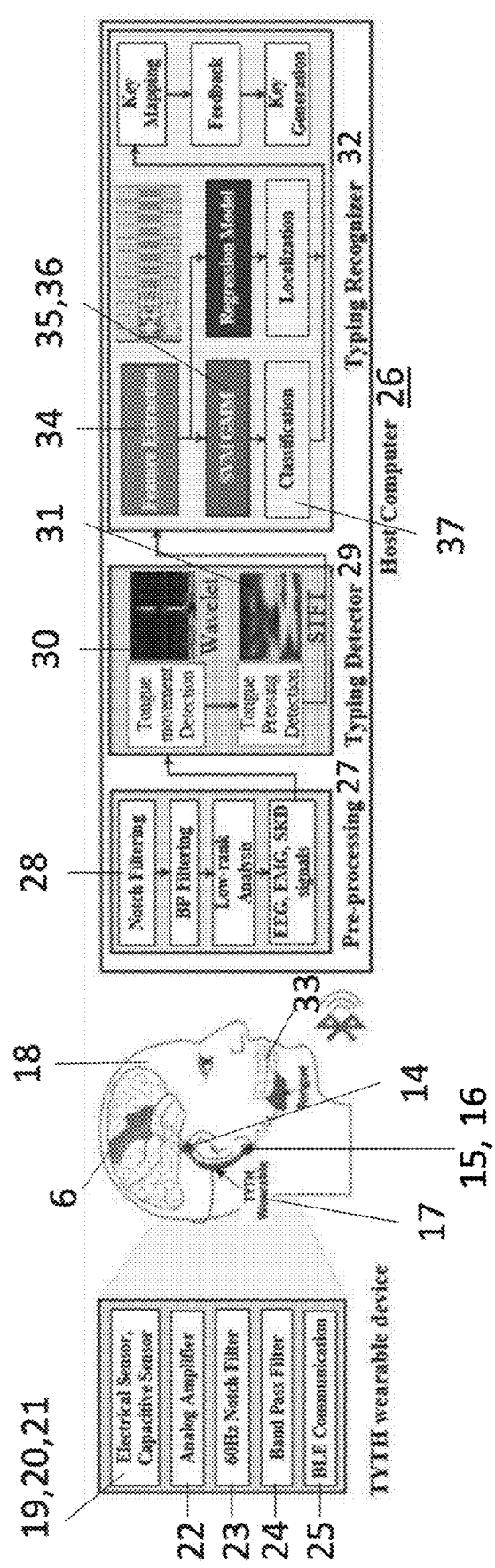
FIG. 5 is an illustration of the components of a tongue-on-teeth typing system.

Now referring primarily to FIG. 5, in particular embodiments, three sensors can be positioned around an outer ear or three sensors can be position around each of the ears of the wearer to capture the EEG, EMG and SKD signals associated with brain activity, muscle contraction, and skin surface deformation. Therefore, in particular preferred embodiments, six sensors (two EEG sensors, two EMG sensors, and two SKD sensors) can be positioned at behind the human outer ear to correspondingly capture EEG signals, EMG signals and SKD signals related to tongue movement or tongue location, or tongue pressing, or combinations thereof.

In particular embodiments, the six sensors can be placed at four locations. One EEG sensors can be placed behind the top of each outer ear to correspondingly capture the EEG signal. One EMG sensor and one SKD sensor can be located or co-located at behind the bottom of the outer ear to correspondingly capture the EMG signal and SKD signals.

Again, referring primarily to FIG. 5, in overview embodiments include one or more of: a wearable device (17) retaining EEG, EMG and SKD sensors (14)(15)(16). The wearable device (17) positions the EEG, EMG and SKD sensors proximate the skin behind the outer ears of the wearer (18). The EEG, EMG and SKD sensors sense a very small electrical potential and skin surface deformation. The EEG, EMG, and SKD signals pass through an analog amplifier (22) to amplify the signals of interest. In particular embodiments, the analog amplifier can have a gain of 24. The wearable device (17) can further includes a notch filter (23) or band-pass filter (24) to remove background electricity noise.

The wearable device (17) can further include BLUETOOTH® or WI-FI® communication (25) to transmit the EEG, EMG and SKD signals to a computing device (26). The computing device receives the streaming data from all the sensors, analyzes them, and predicts the tongue movement, tongue location or pressing area on the teeth on which the tongue presses. The computing device can include a processor communicatively coupled to a non-transitory memory element containing an executable computer code having one or more modules or functions: (1) Pre-processing, (2) Typing Detector, and (3) Typing Recognizer.

Pre-processing components (27) can be used to filter out the environment noises using notch and band-pass filters. A decomposition analysis (28) can be applied to extract the main structure of the EEG or EMG signals, or combinations thereof, to obtain EEG and EMG data.

A typing detector (29) can be used to detect the tongue movement, tongue location or tongue typing event. A wavelet analysis (30) can be applied to capture the tongue movement or location events and Short Time Fourier Transform (STFT)(31) can be applied to detect tongue typing events.

A typing recognizer (32) can be used to recognize which teeth or area the tongue is tapping on. Then, the recognized input can be mapped into a key map to generate the input key and feedback to a user, or wearer of the wearable device (17). As such, disclosed embodiments provide a user with a means to "type" or send commands to a computing devices by tapping on different areas of their teeth or mouth region. Such a system may provide tremendous assistance to individuals who are paralyzed and/or otherwise unable to communicate. For example, as show in FIG. 1, disclosed embodiments may correlate the tongue movement with one of a plurality of tongue location areas. The plurality of tongue location areas may comprise a set of predefined areas. Each predefined areas within the set of predefined areas is associated with particular entry in a key map that interfaces with a computer. For instance, a forward tap towards the upper teeth may correlate with the particular entry of the number "2" or "ABC."

Again, referring primarily to FIG. 5, to differentiate between input data using the wearable device (17) and other interference movement such as talking and eating, a triggering mechanism can be employed by the user to turn on or turn off device input. In particular embodiments, a binary classifier can detect a particular oral movement, such as a "gritting the teeth" event (33). When the user causes a "gritting teeth event," the combined EEG, EMG, and SKD signals (19)(20)(21) have identifiable characteristic(s). This identified characteristic can be used to turn on or turn off device input. Alternatively, the user may be able to turn on or off the device input by performing a particular tongue movement or placing their tongue in a particular tongue location area (e.g., the roof of the mouth).

Bio-signals can be compact and condense representation in some domains called sparsity. Low-rank spare matrix decomposition (low-rank recovery, rank-sparsity incoherence, or similar application) can be used for signal reconstruction in the presence of low signal to noise ratios.

Distorted data (noisy EMG or EEG signals) have a sparse distributed representation among the interested EEG or EMG signals of embodiments of the tongue typing system. The missing data points can be reconstructed by stacking multiple EMG/EEG samples together. If the number of samples is much smaller than the dimension, the observed matrix M is low-rank. Mathematically, it is formulated as the summation of a low-rank cascaded bio electrical matrix ($L_b$) and a sparse noise ($S_n$). To derive the close forms of $L_b$ and $S_n$ from the given matrix (M), minimizes an in-equality constraint ill-posed problem as follows:

$$\text{minimize} \|L_b\|^* + \|S_n\|_1 \, s.t. \, M = L_b + M_n$$

where $\|L_b\|^*$ defines the rank of matrix $L_b$ and $\|L_b^*\|_1$ is the $L_1$ norm $L_b$ and $S_n$ can be recovered by solving a complex optimization problem.

Because low-rank computation only occurs on single dimension, rather than multiple dimensions in image processing, it results in millisecond response even when the algorithm is implemented in compute-intensive software such as MATLAB. RPCA can be applied to input channels including two EEG sensors, two EMG sensors, and two SKD sensors. The EEG and EMG signals can be very weak and require a dedicated signal processing technique to carefully remove the noise while avoiding losing the brain and muscle bio-electric signal activity. The RPCA technique removes most of the high frequency noise in the EEG and EMG signal.

To extract the EEG and EMG data, the sparse vector representing the atoms and their associated weights for the optimal EEG or EMG signals can be recovered by solving the optimization problem. The EEG and EMG signal can be extracted based on the characteristics of the recovered sparse vector. The signatures of the biosignals belonging to the same class can be assumed to approximately lie in a low-dimensional subspace. In order words, the EEG signals related to each movement will lie in one subspace, and the EMG signal will lie into another subspace. Every sequence of bio-signal f(x) can be represented using a basic function with Gabor atoms as follows:

$$f(x) = \sum_{i=1}^{N_D} \delta_i g_i$$

where $N_D$ is the number of atoms in the Gabor dictionary and $g_i$ is one of the atoms in the dictionary here $\delta_i$ is the coefficient of corresponding to g computed by matching pursuit (MP) algorithm. In other words, mixed bio-signals are sparse in the Gabor dictionary. From MP computation results, the first component of the results would include the main structure of the data and the rest presents the details of the data.

$$f(x) = f(x_{main\,structure}) + f(x_{detail\,structure}) \Leftrightarrow f(x) =$$

$$f(x_{EEG\,signal}) + f(x_{EMG\,signal}) + f(x_{noise}) \Leftrightarrow f(x) =$$

$$\sum_{\theta_1}^{\theta_M} \delta_{\theta_i} g_{\theta_i} + \sum_{\theta_{M+1}}^{\theta_N} \delta_{\theta_i} g_{\theta_i} + \sum_{\theta_{N+1}}^{\theta_{N_D}} \delta_{\theta_i} g_{\theta_i}$$

In the above equation, the EEG signal is filled into the main structure of the EEG signal and at lower frequency. The EMG signal and the remaining noise after RPCA represents the detail structure of the signal. The EEG excluded signal is then put into another analysis to extract EMG signal out of the noise signal. The EEG and EMG signal dictionaries can be constructed to ascertain that the signal extracted through matching pursuit implementation will only keep the low frequency components (EEG, EMG). These main structures can be used to detect the tongue pressing event and to recognize the tongue pressing region on the teeth.

Figure 6:
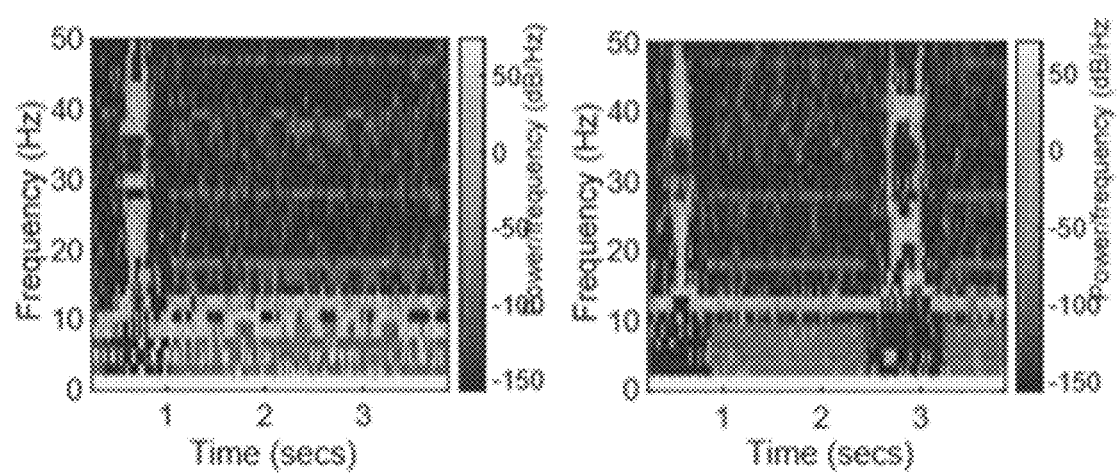
FIG. 6 is a spectrogram of the signal captured at an EEG sensor of the tongue movement one time (LEFT) and two times (RIGHT).
Figure 7:
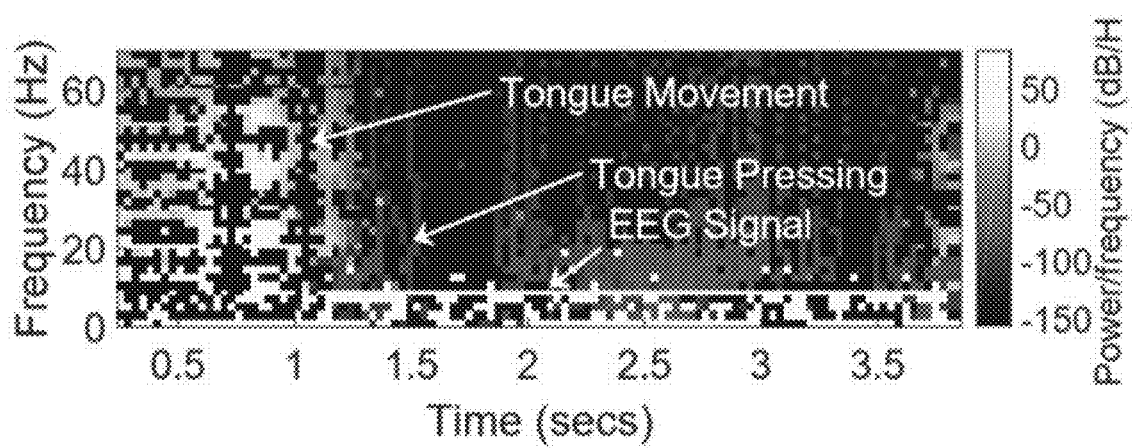
FIG. 7 is a spectrogram of a tongue movement and tongue-on-teeth typing event captured by an EEG sensor.

Now referring primarily to FIGS. 6 and 7, particular embodiments can detect the moment at which the user's tongue presses against a pressing region on the teeth. There are two signatures that are used to detect this movement including 1) the tongue movement, and 2) the presence of the brain signal that controls the tongue. Firstly, wavelet transformation can be applied to detect the discontinuity of the signal where the tongue is moving or pressing against the teeth. Secondly, the system detects the brain signal that controls the tongue which varies from about 10 Hz to about 40 Hz. In particular embodiments, the signal varies from about 8 Hz to about 12 Hz upon the tongue pressing against a tongue pressing region of the teeth. EEG, EMG and SKD sensors (14)(15)(16) can be analyzed by a movement detection algorithm to confirm the tongue movement event. The spectrogram of the EEG signal captured at an EEG sensor location correlates to movement of the tongue one time (LEFT) and two times (RIGHT). In particular embodiments, wavelet coefficient analysis can be used to detect the movement of the tongue at different EEG, EMG or SKD sensors. A majority vote mechanism can be used to validate whether the tongue is pressed or not. A wavelet, denoted by w(t), maintains local information in both the time and frequency domains. It is defined as a waveform that satisfies the following condition:

$$\int_{-\infty}^{+\infty} w(t) dt = 0$$

The wavelet transform uses as the wavelet that satisfies the condition of dynamic scaling and shifting function, $w_{s,p}$, shown below:

$$w_{s,p}(t) = \frac{1}{\sqrt{s}} w\left(\frac{t-p}{s}\right)$$

where $w_{s,p}(t)$ are the integrated and integral transformation signal, s is the scale and p is the shift parameter, which can also be the central location of the wavelet in the time domain. The wavelet can be stretched and translated with flexible windows by adjusting s and p, respectively.

The wavelet transform of the wireless received samples $\tilde{r}(t)$ using transform coefficient W(s,p) is calculated as follows:

$$W(s, p) = \int_{-\infty}^{+\infty} \tilde{r}_f(t) \overline{w_{s,p}}(t) dt = \frac{1}{\sqrt{s}} \int_{-\infty}^{+\infty} \tilde{r}_f(t) \overline{w_{s,p}}\left(\frac{t-p}{s}\right) dt$$

where $\overline{w_{s,p}(t)}$ represents the complex conjugate of $w_{s,p}(t)$. The result of the wavelet transform provides a correlation function of the template signal at different scales (frequency bands) in both the time and frequency domains. The correlation function $w_{s,p}(t)$ has two main features. The first feature is that the time resolution is high with high frequencies while the frequency resolution is high with low frequency signals. When multiplying the high frequency component of the signal with the high frequency of the wavelet, the correlation result will indicate the exact location where the point discontinuity happens. The correlation result can be used to identify a first tongue movement event. The second feature is that as the wavelet has local existence in both time and frequency domain, the point of discontinuity in the signal can be detected with high sensitivity. As the discontinuity (generated by tongue movement) is considered as an event and happens quickly in time, the result of correlation with high frequency wavelet can be readily captured. A tongue movement event can be detected if the majority of the EEG, EMG or SKD sensors detect the movement based upon the corresponding wavelet analysis of EEG, EMG or SKD signals. Tongue movement can be recorded when the coefficient from the result of the wavelet continuous analysis is over a pre-determined threshold event.

As illustrated in FIG. 6, the brain activity signal creates a periodic signal that can be well-reflected in the FFT-based spectrogram at 8-12 Hz. Conversely, a wavelet transform that may be better-suited for capturing transitory phenomena such as a tongue movement may be not well-suited for tongue pressing detection. We formulate the brainwave signal in a form of X sin(2πft+Ø). From the received EEG signal x(t), an efficient approximation of the brain signal activity can identify the dominant frequency E that has a maximum power spectrum density (PSD) through the STFT. Then, the approximation of the brain activity frequency $f_{brain}$ can be as follows:

$$f_{brain} = \max_{[f_{min} \to f_{max}]} \left( \left| \sum_{k=1}^{N} x(t)e^{-j2\pi ftk} \right|^2 \right)$$

where N is the number samples.

After f is estimated, it can be used to estimate the amplitudes and phases of different signals using the following:

$$X = \frac{2}{N} \left| \sum_{k=1}^{N} x(t)e^{-j2\pi ftk} \right|$$

$$\emptyset = \arctan\left( \frac{-\sum_{k=1}^{N} x(t)\sin(2\pi ftk)}{\sum_{k=1}^{N} x(t)\cos(2\pi ftk)} \right)$$

In this way, the system obtains the desired quantities X, Ø, f. The presence of brainwave signal is observable through a short-time Fourier analysis. This event can be confirmed when the maximum power distribution of the peak frequency belongs to the range of 8-12 Hz.

Figure 12:
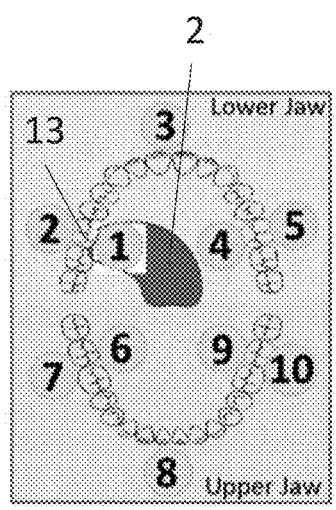
FIG. 12 is an illustration of the tongue pressing areas used in particular embodiments of the system.
Figure 13:
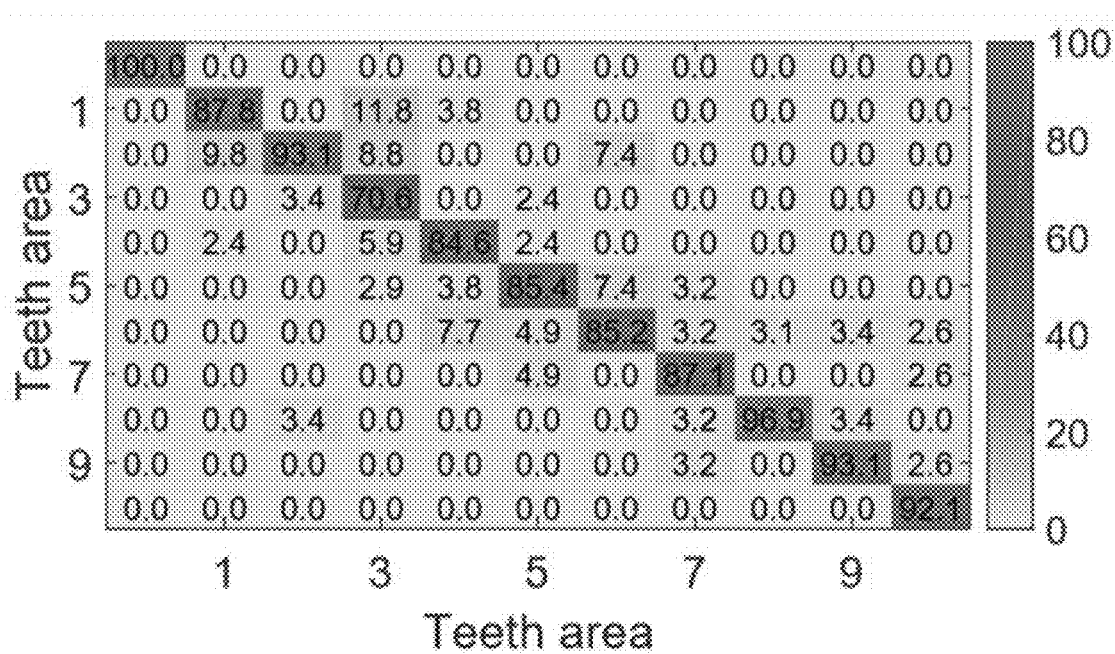
FIG. 13 shows the results of the teeth typing area classification algorithm where teeth area ID 0 is where the use is at rest.

In particular embodiments, an algorithm can be used to accurately recognize correct tongue-teeth pressing areas (13), as shown in FIG. 12. As shown in FIG. 5, the tongue-teeth pressing features can be extracted from the collected EEG and EMG data using the MFCC feature extraction (34) technique. A Gaussian Mixture Model (GMM)(35) can be used to extract the mean vector and final descriptor representation. Finally, a Supported Vector Machine (SVM) algorithm (36) with KBF kernel can be used to classify the data into patterns of tongue movement, location or tongue teeth pressing areas (13). The pattern of tongue pressing on teeth pressing areas (13) can be defined by the EEG, EMG and SKD signals (19)(20)(21) captured from EEG, EEG and SKD sensors (14)(15)(16) (the example includes six sensors positioned as above describe with a sample speed of about 1500 samples per second).

The resulting data can be overlappingly sliced windows using a Hamming window. Then each window goes through the feature extraction process where it is convolved with a filter bank to obtain the coefficients as feature vectors. The Mel filter bank or Mel-frequency cepstral coefficients (MFCC) can be used to process the signals. At this point, a matrix can be constructed of MFCC features (34) where the number of rows corresponds to the number of windows and the columns correspond to the dimension of MFCC features. Here, the Mel-coefficients and the first and second order derivatives can be applied to extend the feature space. In particular embodiments, the combination of Mel-coefficients, delta and double delta can be an improvement as compared to the results of using only Mel-coefficients alone.

Each sample can be represented by a set of MFCC features, and the distribution of these feature points can be used to estimate the Gaussian Mixture Model (GMM) and extract the mean vector for the final descriptor representation. Estimating the GMM from a set of data points can be achieved by 1) initializing the parameters of distribution, and 2) using the Expectation Maximization (EM) algorithm to adjust the model to fit the feature points. In this respect Random initialization may not be effective for the EM to converge to an optimal point, especially in the context of using bio-electrical signals. In some embodiments, a Universal Background Model (UBM) can be used for the initialization step.

The UBM model is a GMM model but is trained on the entire dataset. Therefore, using this model for initialization may help to generalize the problem characteristics, and thus helps the GMM adaptation to quickly converge. The processes of obtaining the GMM model based on UBM can be summarized in two stages: 1) using the EM algorithm for the entire dataset of samples to obtain the UBM model, and 2) using the Maximum a Posteriori Estimation to fit the UBM with the feature points of each sample to create the specific GMM model for the particular sample. The above procedure can be applied separately to the data resulting from each of the sensors (in the illustrative example six sensors generate six channels of data for one tongue posture). The use of multiple sensors to produce multiple discrete channels can significantly improve performance when the kernels of six discrete channels are averaged; however, this is not intended to preclude embodiments having fewer than six discrete channels.

Finally, the data can be classified by a Support Vector Machine with different kernels. In particular embodiments, three basic kernels can be utilized: linear, cosine and RBF. The above classification algorithm provides identifiable "tongue pressing areas" which can be distinguished from one another. In particular embodiments, a localization algorithm can be applied to continuously track the tongue pressing locations even at untrained areas. Different teeth require different activation muscles as well as brain activity. The localization algorithm builds a regression function that correlates the input bio-signal to an output x,y,z coordinate of each tooth or tongue pressing area.

Figure 8:
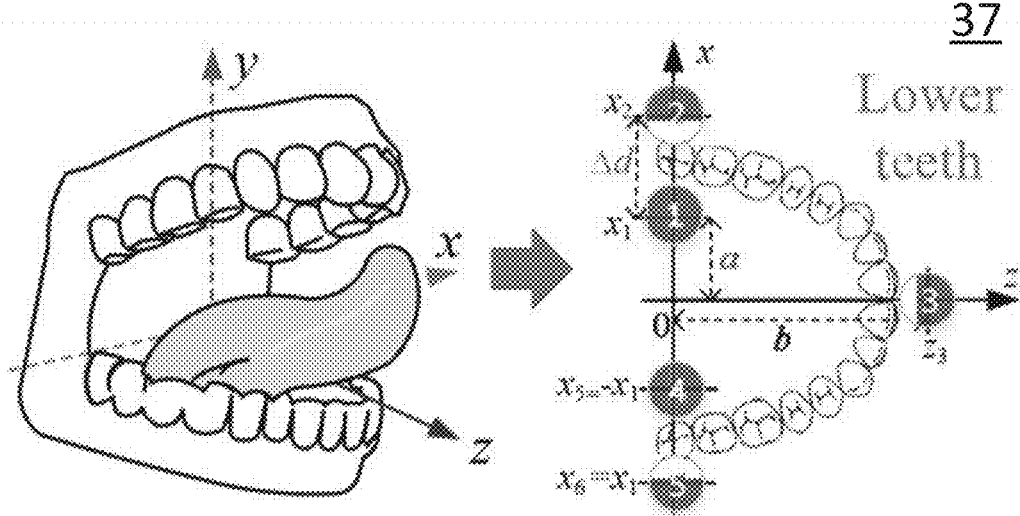
FIG. 8 illustrates the coordinate system of each of the six locations of the lower teeth.

Now referring primarily to FIG. 8, an illustrative coordinate system (37) includes six locations of the lower teeth. In this illustrative example, the root of the tongue has the coordinate of 0(0,0,0), the distance between the middle of the tongue to the left teeth is "a", to the front teeth is "b", to the upper teeth is "c", and the distance between inside and outside teeth is "Δd", the coordinate of each location of interest can be represented as: 1($x_1$, 0, 0)≈1(a, 0, 0). Similarly, we can convert the location at the upper teeth with an assumed distance c from the lower teeth.

Based on these relationships, a regression model can approximate the x,y,z coordinate of a certain tongue pressing location based on the input from featured signal. Because the GMM has 42 dimensions in total, direct mapping to a three-dimensional location can require an intermediate step that transforms a high dimensional feature GMM into a three-dimensional coordinate. In particular embodiments, the informative level of each feature dimension can be compared to select the best three representative ones. Using the Principal Components Analysis (PCA), we can select the coordinates that represent our data, in particular embodiments, the top three coordinates can be utilized.

For example, the whole features may be used to extract the coefficient matrix of the PCA. Then each feature vector can be multiplied with the first three columns of the coefficient matrix to project it onto the three-dimensional space to construct a reference projection between feature coordinate and real world coordinate for regression analysis. We then apply a linear regression model to interpolate the relation between our ground truth data and the mapping feature location. A resulting non-linear regression model can be approximated by a linear model using Taylor's theorem. The regression model can be applied to a small fixed set of features from the original data and not to raw data.

Figure 9:
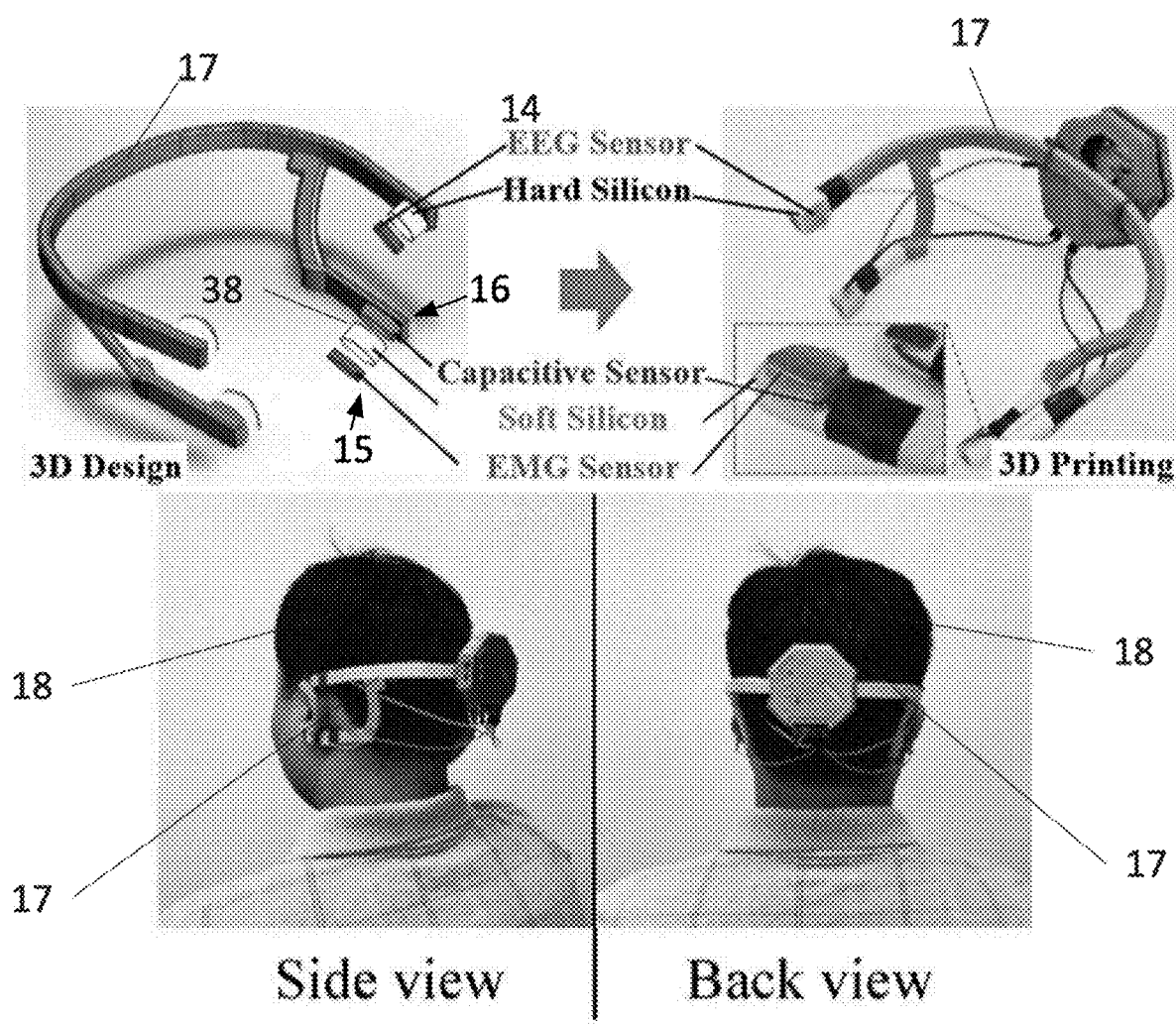
FIG. 9 is an illustration of a particular embodiment of a wearable device including EEG, EMG and SKD sensors.
Figure 11:
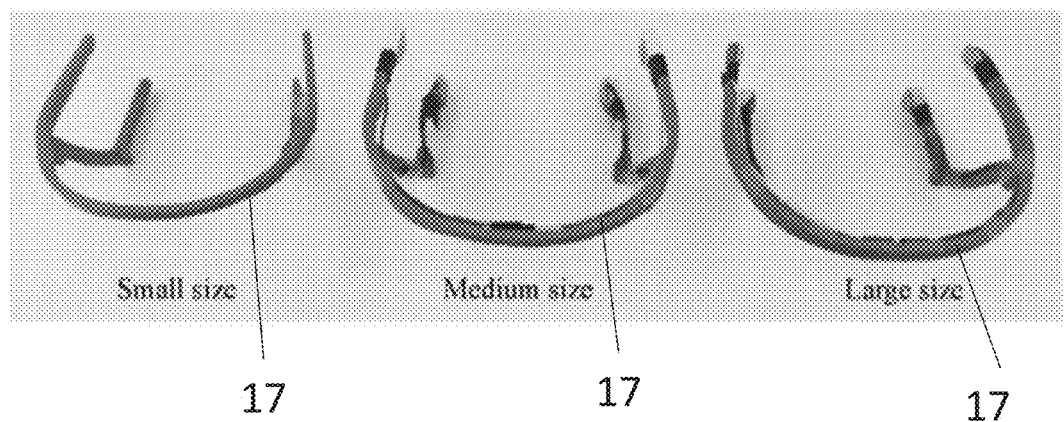
FIG. 11 is an illustration showing the scalability of particular embodiments of the wearable device.

Now referring primarily to FIGS. 9 and 11, embodiments of the wearable device (17) can comprise a sufficiently resiliently flexible material to maintain contact between the EEG, EMG and SKD sensors (14)(15)(16) and the skin of the wearer (18). In particular embodiments, a copper tape electrode can directly contact the skin and the sensor. In particular embodiments, the EEG sensor can contact the skin of the wearer behind the top of the outer ear and the EMG and SKD sensors can contact the skin of the wearer behind the bottom of the outer ear. In particular embodiments the EMG and SKD sensors can be co-located.

In the illustrative embodiment of FIG. 9, the two top sensors (one behind each ear) can be used to capture the EEG signal (19) from the human brain and, the two bottom sensors (one behind each ear) can be used to capture the EMG signal (20) generated by tongue's extrinsic muscles (9). These sensors can further be placed on a silicon layer (38) (of about 1 mm thickness) to create contact between the sensor and the skin of the wearer. To measure the EEG or the EMG signal, a combination differential input and output amplifiers can be used.

Figure 10:
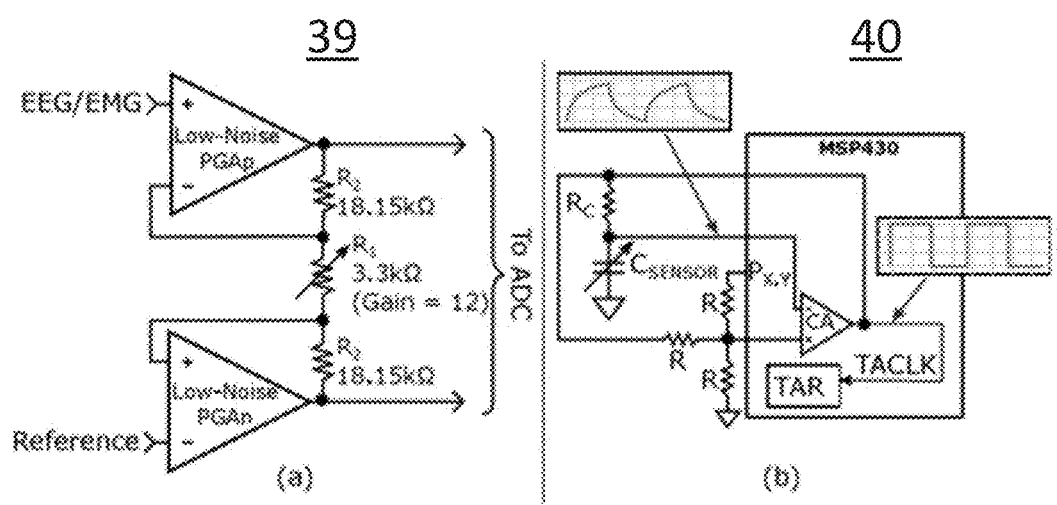
FIG. 10 is a schematic circuit diagram including a programmable gain amplifier.

Now referring primarily to FIG. 10, a suitable programmable gain amplifier can be a CMOS chip model ADS1299. ADS1299 can be used to measure the electric potential generated by brain and muscle contraction activities. ADS1299 supports programmable gain amplifier (PGA) of 1, 2, 4, 6, 8, 12, and 24). The ADCs can support about 250 samples/s to about 16 k samples/s.

Again, referring primarily to FIGS. 9 and 10, capacitive sensing can be used to estimate physical properties such as touch, proximity, and deformation by measuring the capacitance between two or more conductors. These conductors can comprise conductive materials including or consisting of metal, foils, transparent films, plastics, rubbers, textiles, inks, paints, or human body, or combinations thereof. Capacitive sensing characteristics can be exploited to measure the skin surface deformation caused by tongue movement.

A capacitance exists whenever two electrodes are separated from each other by a distance $\Delta d$. In the illustrative example, the copper tape can be separated from a human skin by a soft and deformable silicon Ecoflex 00-10 from Smooth On at about 1 mm. At the bottom electrodes on each ear, there can be another electrode at another side of the flexible form to capture the skin surface deformation caused by tongue movements. The tongue movement will create a distance changes between the two side of the flexible form. In particular embodiments, the movement can be captured using a piezoelectric sensor or an accelerometer. However, in preferred embodiments capacitive sensing can be used to capture the miniscule movement of the skin caused by the tongue behavior.

In the example, the distance changes between the two electrodes, one on the skin and the other on the wearable device, are measured. At a stable condition, the capacitance created by two metal plates can be calculated as $C=\in_0\in_r A/d$, where C is the capacitance in Farads, A is the area in meters square, d is distance between two plates in meters, and $\in$ is dielectric constant, which is the product of free space $\in_0$ and relative dielectric constant of the material, $\in_r$.

When the tongue movement occurs, the skin surface deforms, the flexible material in the middle of two copper plates create a change in their area and distance. This generates a change in capacitance which can be measured by the capacitive sensor. Now referring primarily to FIG. 10b, a schematic of a relaxation oscillator suitable for use in embodiments of the invention is shown. Any change in capacitance at the measurement pin $C_{sensor}$ can be captured using internal Timer A of the MSP4305969 circuit. The R ladder network creates a reference for comparator that changes with its input when Px.y is high. This reference is opposite in polarity to the charge or discharge of the $C_{sensor}$, resulting in a continuous oscillation. With equal R, the frequency of oscillation is obtained by $f_{osc}=1/[1.386\times R\times C]$. $f_{osc}$ can be obtained by counting the oscillation periods over a fixed duration. Then, C sensor is measured through fosc. In this example, Rc=100 k$\Omega$ may be used.

Turning now to some illustrative, but non-limiting examples:

EXAMPLE 1: A particular embodiment can be practiced using an open BCI board for EEG and EMG data collection. To measure the capacitance variation created by the skin surface deformation a MSP430FR5969 module can be used. Both devices can communicate to a Lenovo ThinkPad T570 laptop through Bluetooth Low Energy device at 115200 baud rate. The open BCI can be sampled at a sampling rate of up to about 250 Hz, and the MSP430FR5969 can be sampled at about 10 Hz. The data from open BCI can be streamed to a laptop computer through Lab Streaming Layer (LSL) network protocol written on python. The pre-processing and algorithms are implemented on Matlab R2017b. The Matlab and Python data are exchanged using a basic TCP protocol. The signal de-noising, extraction, classification (SVM GMM), localization algorithm can be implemented on Matlab.

EXAMPLE 2: To evaluate the performance of disclosed systems, an experiment was conducted over fifteen participants in a normal office environment. The participants' demographic is summarized in Table 1.

TABLE 1

Participants' demographic description
Participant Demographics

| | |
|---|---|
| Age (years) | 18-35 years old |
| Gender Ratio | Male: 11, Female: 4 |
| Head size use | Small: 3, Medium: 8, Large: 4 |

In the experimental setup, the wearer was fitted with the wearable device shown in FIG. 9. Specifically, as shown in FIG. 9 (RIGHT), the 2 pairs of copper-tape sensors were placed behind the participant's ears in the left and right sides to collect the signals of interest (EEG, EMG, and SKD signals). The wearable device does not generate any signal to affect the user, it just passively listens to the bioelectrical signals generated by the brain and the tongue muscles, and the capacity change caused by the skin surface deformation. A camera recorded the user's tongue gestures for ground truth data.

After the wearable device was correctly position on the wearer, the user sat in front of a monitor that instructed him on when to perform a gesture and when to rest his tongue. For each gesture, the wearer required approximately three seconds for performing a gesture. Additionally, each wearer was asked to perform ten gestures, twenty times for each gesture. FIG. 12 is an illustration of the tongue pressing areas used in particular embodiments of the system. The wearers were required to consciously follow the instruction on the screen and to perform the gestures. For example, when the screen says "Press," the user pressed his or her tongue to a requested location. When the screen says "Release," the user released his or her tongue from pressing. The duration between Press and Release was about 1.5 seconds. The data collection duration of each wearer varied from about forty-five minutes to about seventy-five minutes.

The data collected from fifteen participants was used to evaluate the system. Each wearer performed ten typing and one resting gesture. Each gesture was repeated twenty times. As such, there were three-thousand and three hundred total samples taken. Each epoch contained a matrix of six columns representing signal from six sensors (two EEG, two EMG, and two SKD). Seventy-five percent of the data was used for training and the remaining twenty-five percent of data was used for testing. The results depicted are the average accuracy for the whole data set collected.

Figure 16:
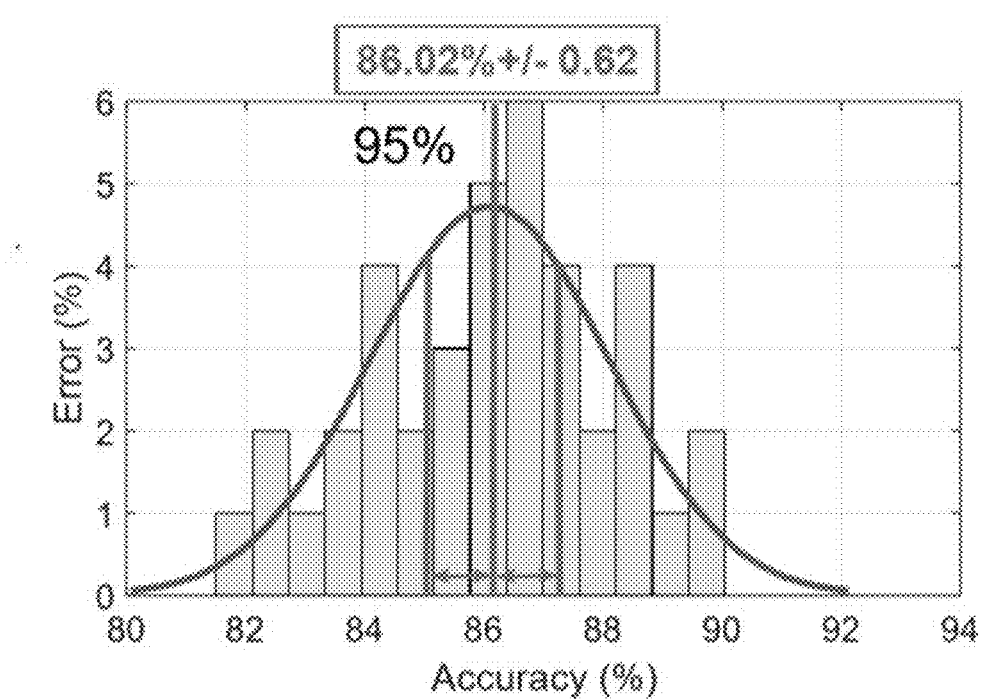
FIG. 16 is a graph which evidences the confidence level of the classification algorithm.

FIG. 16 is a graph which evidences the confidence level of the classification algorithm. The results of the teeth typing area classification algorithm are depicted where Teeth Area ID 0 correlates to wearer at rest. Embodiments of the system can obtain about ninety-six percent accuracy in detecting a specific tongue pressing area while the overall accuracy can be about eighty-eight percent. More specifically, the results suggest that the performance of the system depends on the location on the teeth the wearer types. The performance of the location outside the teeth including 2, 4, 6, 8, 10 can obtain better performance compared with insides areas.

Figure 14:
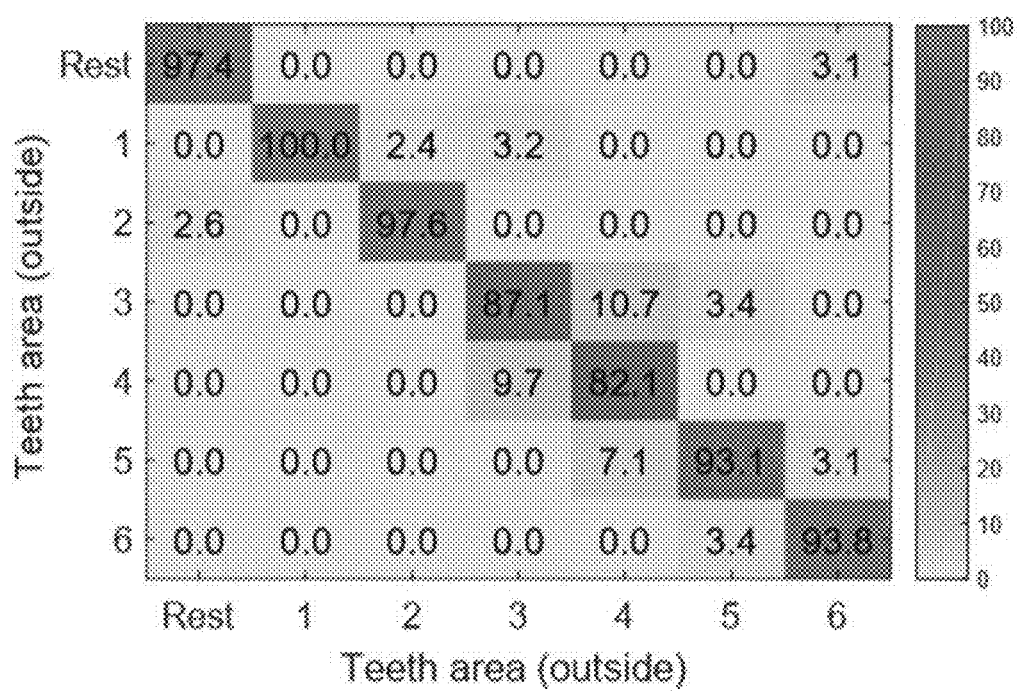
FIG. 14 illustrates the performance of a particular embodiment of the wearable device in performing six outside tooth pressing areas shown in FIG. 12 as ID 2, 4, 6, 8, 10.
Figure 15:
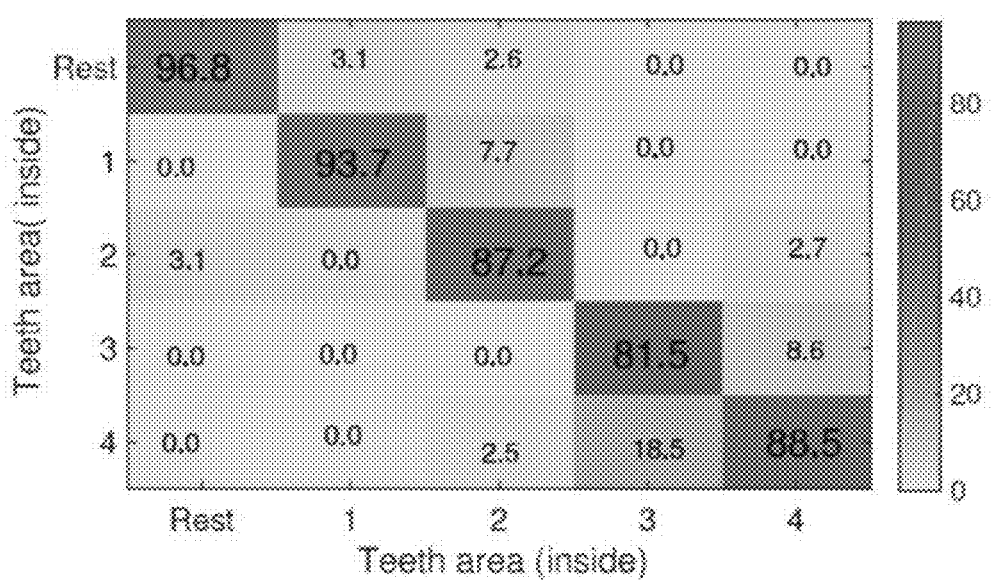
FIG. 15 illustrates the performance of a particular embodiment of the wearable device in performing four inside tooth pressing areas shown in FIG. 12 as ID 1, 3, 5, 7.

FIG. 14 illustrates the performance of a particular embodiment of the wearable device in performing six outside tooth pressing areas shown in FIG. 12 as ID 2, 4, 6, 8, 10. The performance inclusive of six outside area (ID 2, 4, 6, 8, 10 in FIG. 12) was greater with average accuracy of about ninety-three percent. The performance accuracy inclusive of the inside teeth locations (ID 1, 3, 5, 7) was about eighty-nine percent. This matches the wearers stated experience in that performing the typing at outside areas was easier than the inside ones.

Now referring again to FIG. 16, the confidence level of the classification algorithm was confirmed at ninety-five percent with the accuracy of about eighty-six percent and with a variance within 0.62 interval.

Figure 17:
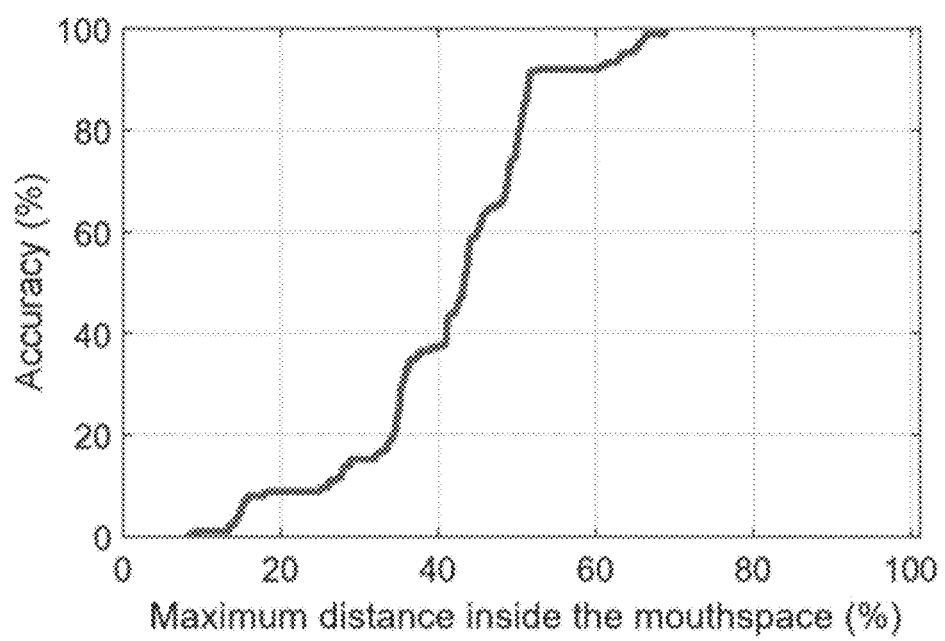
FIG. 17 is a graph of results of a particular embodiment of the wearable device which plots accuracy against maximum distance inside the mouth space.

FIG. 17 is a graph of results of a particular embodiment of the wearable device which plots accuracy against maximum distance inside the mouth space. The results of regression are shown for the localization model for ten trained locations. Assuming a normal human mouth size as the input for the regression, and that the distance from the root of the tongue to each location is around 3 cm, the system can locate a tongue pressing location with 4.5 cm error range (3×3×3 is the maximum error range) at the accuracy of about ninety percent.

Figure 18:
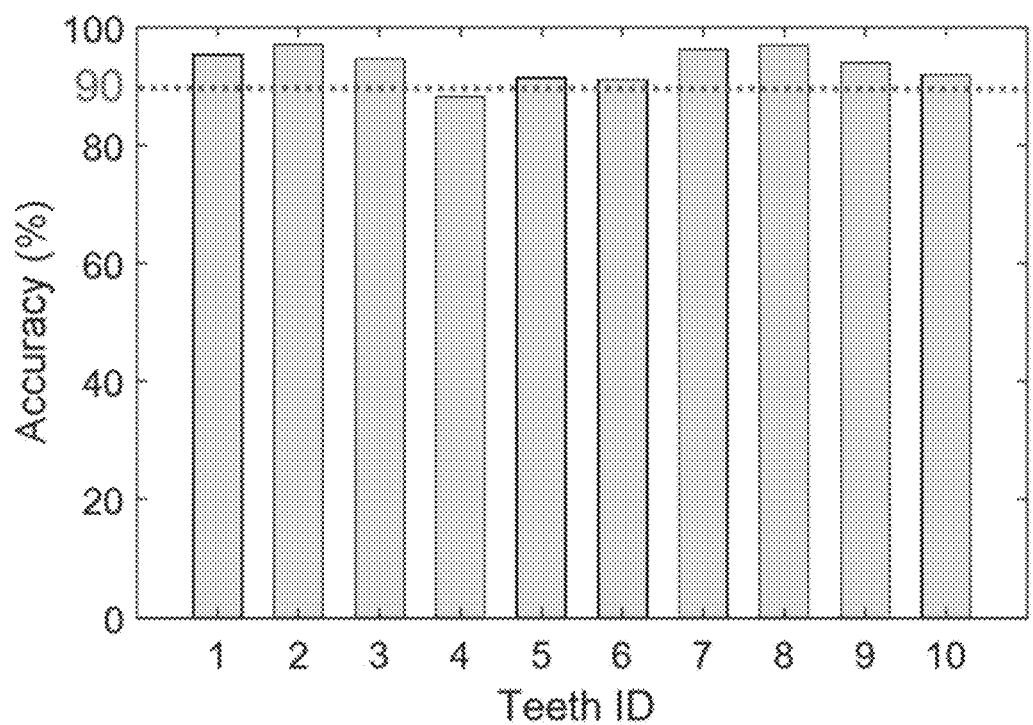
FIG. 18 is graph of results of a particular embodiment of the wearable device which plots accuracy in terms of detecting a particular tongue tooth typing event.

Now referring primarily to FIG. 18, the performance of the system in terms of detecting the tongue pressing event was evaluated using the combined data that contains the tongue pressing event and the tongue relax data with fifty-fifty ratio. The system obtains up to about ninety-seven percent of accuracy in terms of detecting the typing event using the binary classifier built from wavelet and short-time Fourier transform.

Figure 19:
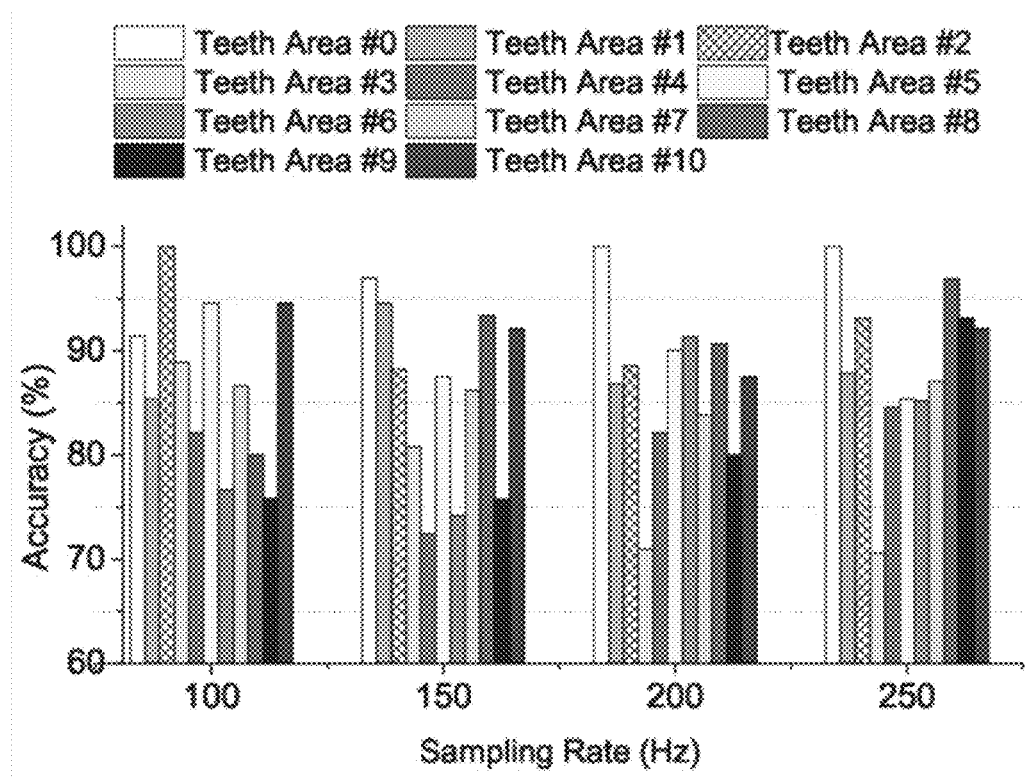
FIG. 19 is a graph of results of a particular embodiment of the wearable device which plots accuracy again sampling rate.

FIG. 19 is a graph of results of a particular embodiment of the wearable device which plots accuracy again sampling rate. The sampling rate represents the details of the signal that the system could capture. Higher sampling rate also means capture of more noise from the environment. Sampling rates were varied from 100 Hz to 250 Hz. While the system's performance varies at different sampling rates the overall performance can be substantially constant (86-88%). Note that the system does not converge when the sample rate is reduced to 50 Hz.

Figure 20:
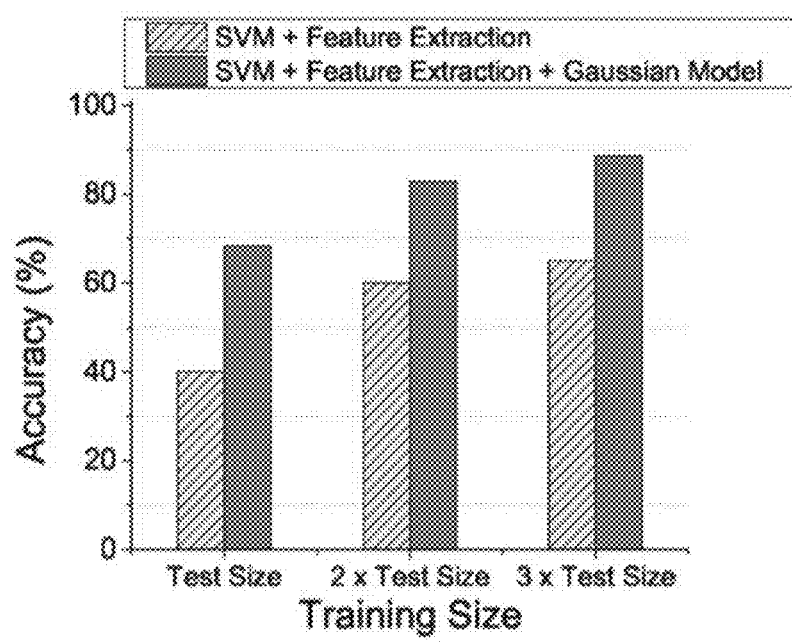
FIG. 20 is a graph of results of a particular embodiment of the wearable device which plots accuracy again training test size.

Now referring primarily to FIG. 20, which illustrates the impact on the Gaussian Model when the size of the testing data is fixed and the size of the training data varies. Embodiments having training size three times larger than the testing size achieved better results. In addition, without GMM, the system only obtains up to about 67% compared with about 88% when using GMM. Also, the selection of kernel SVM is also important and defines the accuracy of the system. Additionally, different types of kernel for classification purposes can be selected including 1) Linear, 2) Cosine, and 3) RBF. The performance of RBF can be superior to linear or cosine.

Figure 21:
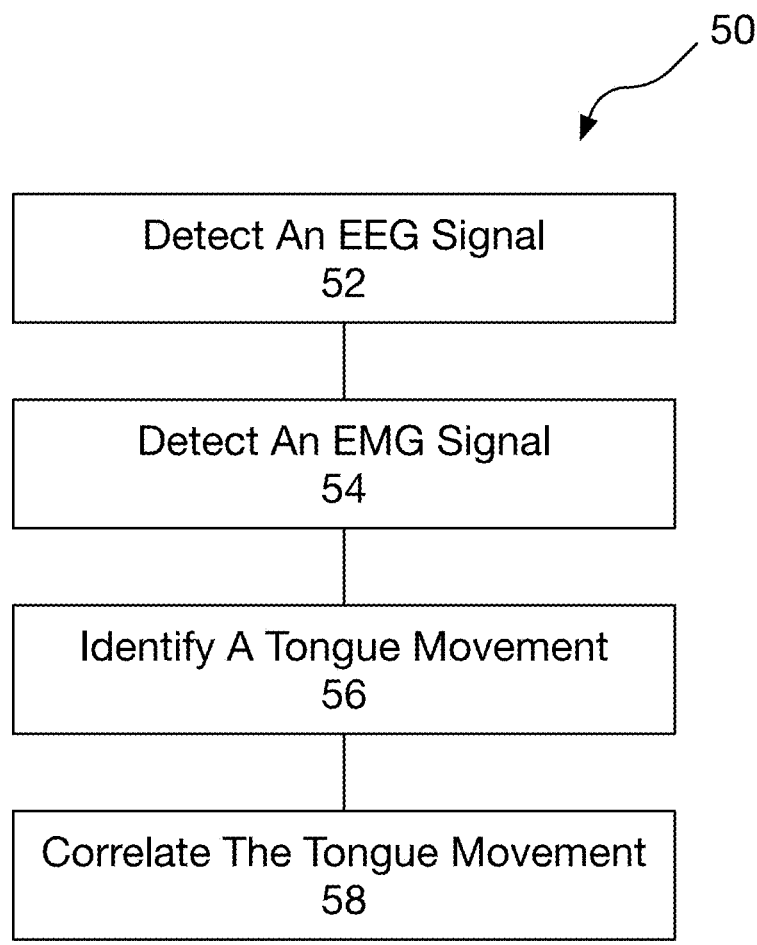
FIG. 21 is a flowchart of a method for identifying tongue movement.

FIG. 21 is a flowchart of a method 50 for identifying tongue movement. The depicted method includes an act 52 of detecting an EEG signal. Act 52 comprises detecting an electroencephalography ("EEG") signal from an EEG sensor, wherein the EEG sensor configured to sense the EEG signal generated by a brain in association with a tongue movement. The method 50 also includes an act 54 of detecting an EMG signal. Act 54 comprises detecting an EMG signal from an EMG sensor, wherein the EMG sensor configured to sense the EMG signal generated by cranial nerve stimulation of muscles associated with the tongue movement. For example, FIGS. 1, 5, and 9, and the accompanying description, describe the usage of EEG sensors and EMG sensors to tracking the movement of the tongue.

Additionally, method 50 includes an act 56 of identifying a tongue movement. Act 56 includes identifying the tongue movement based on the EEG signal and the EMG signal. Further, method 50 includes an act 58 of correlating the tongue movement. Act 58 comprises correlating the tongue movement with one of a plurality of tongue location areas. For example, FIGS. 1, 6, 7, and 8, and their associated descriptions, describe the correlating of a tongue to particular movements and areas.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for identifying tongue movement, comprising:
   an electroencephalography ("EEG") sensor configured to sense an EEG signal generated by a brain in association with a tongue movement;
   an electromyography ("EMG") sensor configured to sense an EMG signal generated by cranial nerve stimulation of muscles associated with the tongue movement;
   one or more processors; and
   one or more computer-readable media having stored thereon executable instructions that when executed by the one or more processors configure the computer system to perform at least the following:
     detect the EEG signal from the EEG sensor;
     detect the EMG signal from the EMG sensor;
     based on the EEG signal and the EMG signal, identify the tongue movement; and
     correlate the tongue movement with one of a plurality of tongue location areas.

2. The computer system of claim 1, further comprising a skin deformation (SKD) sensor configured to sense a SKD signal that varies based on skin deformation.

3. The computer system of claim 2, wherein the EEG sensor, the EMG sensor, and the SKD sensor comprise a pair of EEG sensors, a pair of EMG sensors, and a pair of SKD sensors.

4. The computer system of claim 1, wherein the executable instructions include instructions that are executable to configure the computer system to:
   detect the SKD signal from the SKD sensor;
   based on the SKD signal, the EEG signal and the EMG signal, identify the tongue movement; and
   correlate the tongue movement with one of the plurality of tongue location areas.

5. The computer system of claim 1, wherein the plurality of tongue location areas comprise a set of predefined areas.

6. The computer system of claim 5, wherein each predefined areas within the set of predefined areas is associated with particular entry in a key map that interfaces with a computer.

7. The computer system of claim 5, wherein at least one predefined areas within the set of predefined areas is associated with the tongue movement articulating outside a user's teeth.

8. The computer system of claim 1, wherein the executable instructions include instructions that are executable to configure the computer system to:
   detect the EEG signal and the EMG signal;
   based on the EEG signal and the EMG signal, identify a particular oral movement; and
   correlate the particular oral movement to a command to start or stop said computing device.

9. The computer system of claim 8, wherein the particular oral movement comprises a teeth-gritting event.

10. The computer system of claim 8, wherein the particular oral movement comprises correlating the tongue movement with a particular tongue location area.

11. A computer-implemented method for identifying tongue movement, the computer-implemented method executed on one or more processors, the computer-implemented comprising:
    detecting an electroencephalography ("EEG") signal from an EEG sensor, wherein the EEG sensor configured to sense the EEG signal generated by a brain in association with a tongue movement;
    detecting an EMG signal from an EMG sensor, wherein the EMG sensor configured to sense the EMG signal generated by cranial nerve stimulation of muscles associated with the tongue movement;
    based on the EEG signal and the EMG signal, identifying the tongue movement; and
    correlating the tongue movement with one of a plurality of tongue location areas.

12. The computer-implemented method of claim 11, further comprising a skin deformation (SKD) sensor configured to sense a SKD signal that varies based on skin deformation.

13. The computer-implemented method of claim 12, wherein the EEG sensor, the EMG sensor, and the SKD sensor comprise a pair of EEG sensors, a pair of EMG sensors, and a pair of SKD sensors.

14. The computer-implemented method of claim 11, further comprising:
    detecting the SKD signal from the SKD sensor;
    based on the SKD signal, the EEG signal and the EMG signal, identifying the tongue movement; and
    correlating the tongue movement with one of the plurality of tongue location areas.

15. The computer-implemented method of claim 11, wherein the plurality of tongue location areas comprise a set of predefined areas.

16. The computer-implemented method of claim 15, wherein each predefined areas within the set of predefined areas is associated with particular entry in a key map that interfaces with a computer.

17. The computer-implemented method of claim 11, further comprising:
    detecting the EEG signal and the EMG signal;
    based on the EEG signal and the EMG signal, identifying a particular oral movement; and correlating the particular oral movement to a command to start or stop said computing device.

18. The computer-implemented method of claim 17, wherein the particular oral movement comprises a teeth-gritting event.

19. The computer-implemented method of claim 17, wherein the particular oral movement comprises correlating the tongue movement with a particular tongue location area.

20. A computer program product comprising one or more computer storage media having stored thereon computer-executable instructions that, when executed at a processor, cause the computer system to perform a method for identifying tongue movement, the method comprising:
- detecting an electroencephalography ("EEG") signal from an EEG sensor, wherein the EEG sensor configured to sense the EEG signal generated by a brain in association with a tongue movement;
- detecting an EMG signal from an EMG sensor, wherein the EMG sensor configured to sense the EMG signal generated by cranial nerve stimulation of muscles associated with the tongue movement;
- based on the EEG signal and the EMG signal, identifying the tongue movement; and
- correlating the tongue movement with one of a plurality of tongue location areas.

* * * * *